United States Patent [19]

Buss et al.

[11] 4,434,311

[45] Feb. 28, 1984

[54] CONVERSION OF ALKYCYCLOPENTANES TO AROMATICS

[75] Inventors: Waldeen C. Buss, Kensington; Thomas R. Hughes, Orinda, both of Calif.

[73] Assignee: Chevron Research Company, San Francisco, Calif.

[21] Appl. No.: 420,541

[22] Filed: Sep. 20, 1982

Related U.S. Application Data

[63] Continuation-in-part of Ser. No. 344,570, Feb. 1, 1982, abandoned, and a continuation-in-part of Ser. No. 344,572, Feb. 1, 1982.

[51] Int. Cl.$^3$ ............................................. C07C 2/64
[52] U.S. Cl. .................................... 585/444; 585/430
[58] Field of Search ................................. 585/430, 444

[56] References Cited

U.S. PATENT DOCUMENTS 3,783,123  1/1974  Young ............................. 252/455 Z Primary Examiner—Curtis R. Davis
Attorney, Agent, or Firm—D. A. Newell; S. R. LaPaglia; E. A. Schaal

[57] ABSTRACT

A method is disclosed for the dehydroisomerization of alkylcyclopentanes using a catalyst comprising a large-pore zeolite, a Group VIII metal, and an alkaline earth metal.

15 Claims, No Drawings

CONVERSION OF ALKYCYCLOPENTANES TO AROMATICS

CROSS-REFERENCE TO RELATED APPLICATION

This is a continuation-in-part of application Ser. No. 344,570, filed Feb. 1, 1982, and now abandoned, and application Ser. No. 344,572, filed Feb. 1, 1982.

BACKGROUND OF THE INVENTION

The invention relates to a new catalyst and a method using that catalyst in reforming hydrocarbons, more particularly dehydroisomerization of alkylcyclopentanes to form the corresponding aromatic hydrocarbons.

Catalytic reforming is well known in the petroleum industry and refers to the treatment of naphtha fractions to improve the octane rating by the production of aromatics. The more important hydrocarbon reactions occurring during reforming operation include dehydrogenation of cyclohexanes to aromatics, dehydroisomerization of alkylcyclopentanes to aromatics, and dehydrocyclization of acyclic hydrocarbons to aromatics. A number of other reactions also occur, including the following: dealkylation of alkylbenzenes, isomerization of paraffins, and hydrocracking reactions which produce light gaseous hydrocarbons, e.g., methane, ethane, propane and butane. Hydrocracking reactions are to be particularly minimized during reforming as they decrease the yield of gasoline boiling products.

Because of the demand for high octane gasoline for use as motor fuels, etc., extensive research is being devoted to the development of improved reforming catalysts and catalytic reforming processes. Catalysts for successful reforming processes must possess good selectivity, i.e., be able to produce high yields of liquid products in the gasoline boiling range containing large concentrations of high octane number aromatic hydrocarbons and accordingly, low yields of light gaseous hydrocarbons. The catalysts should possess good activity in order that the temperature required to produce a certain quality product need not be too high. It is also necessary that catalysts possess good stability in order that the activity and selectivity characteristics can be retained during prolonged periods of operation.

Catalysts comprising platinum, for example, platinum supported on alumina, are well known and widely used for reforming of naphthas. The most important products of catalytic reforming are benzene and alkylbenzenes. These aromatics hydrocarbons are of great value as high octane number components of gasoline.

Catalytic reforming is also an important process for the chemical industry because of the great and expanding demand for aromatic hydrocarbons for use in the manufacture of various chemical products such as synthetic fibers, insecticides, adhesives, detergents, plastics, synthetic rubbers, pharmaceutical products, high octane gasoline, perfumes, drying oils, ion-exchange resins, and various other products well known to those skilled in the art. One example of this demand is in the area of chlorination of benzene to given chlorobenzene which is then used to prepare phenol by hydrolysis with sodium hydroxide. The chief use for phenol is in the manufacture of phenol-formaldehyde resins and plastics. Another route to phenol uses cumene as a starting material and involves the oxidation of cumene by air to cumene hydroperoxide which can then be decomposed to phenol and acetone by the action of an appropriate acid. The demand for ethylbenzene is primarily derived from its use to manufacture styrene by selective dehydrogenation; styrene is in turn used to make styrene-butadiene rubber and polystyrene. Ortho-xylene is typically oxidized to phthalic anhydride by reaction in vapor phase with air in the presence of a vanadium pentoxide catalyst. Phthalic anhydride is in turn used for production of plasticizers, polyesters and resins. The demand for para-xylene is caused primarily by its use in the manufacture of terephthalic acid or dimethylterephthalate which in turn is reacted with ethylene glycol and polymerized to yield polyester fibers. Substantial demand for benzene also is associated with its use to produce aniline, Nylon, maleic anhydride, solvents and the like petrochemical products. Toluene, on the other hand, is not, at least relative to benzene and the $C_8$ aromatics, in great demand in the petrochemical industry as a basic building block chemical; consequently, substantial quantities of toluene are hydrodealkylated to benzene or disproportionated to benzene and xylene. Another use for toluene is associated with the transalkylation of trimethylbenzene with toluene to yield xylene.

Responsive to this demand for these aromatic products, the art has developed and industry has utilized a number of alternative methods to produce them in commercial quantities. One response has been the construction of a significant numer of catalytic reformers dedicated to the production of aromatic hydrocarbons for use as feedstocks for the production of chemicals. As is the case with most catalytic processes, the principal measure of effectiveness for catalytic reforming involves the ability of the process to convert the feedstocks to the desired products over extended periods of time with minimum interference of side reactions.

The dehydrogenation of cyclohexane and alkylcyclohexanes to benzene and alkylbenzenes is the most thermodynamically favorable type of aromatization reaction of catalytic reforming. This means that dehydrogenation of cyclohexanes can yield a higher ratio of (aromatic product/nonaromatic reactant) than either of the other two types of aromatization reactions at a given reaction temperature and pressure. Moreover, the dehydrogenation of cyclohexanes is the fastest of the three aromatization reactions. As a consequence of these thermodynamic and kinetic considerations, the selectivity for the dehydrogenation of cyclohexanes is higher than that for dehydroisomerization or dehydrocyclization. Dehydroisomerization of alkylcyclopentanes is somewhat less favored, both thermodynamically and kinetically. Its selectivity, although generally high, is lower than that for dehydrogenation. Dehydrocyclization of paraffins is much less favored both thermodynamically and kinetically. In conventional reforming, its selectivity is much lower than that for the other two aromatization reactions.

It is well known that the naphthenic hydrocarbons having $C_6$-rings can be easily and quite selectively dehydrogenated to the corresponding aromatic hydrocarbons with good conversion and yields. The naphthenes having $C_5$-rings, on the other hand, cannot be so converted by dehydrogenation alone. In the first place, they are much more susceptible to cracking. In the second place, the reaction of the $C_5$-ring naphthenes to aromatics is not a simple dehydrogenation. Thus, the selective dehydrogenation of $C_6$-ring naphthenes in the presence of alkyl $C_5$-ring naphthenes with nonacidic platinum catalysts has been extensively investigated with the conclusion that the reaction is sufficiently specific to the $C_6$-ring naphthenes to be useful as an analytical tool for determining the concentration of $C_6$-ring naphthenes.

SUMMARY OF THE INVENTION

The present invention uses a catalyst comprising a large-pore zeolite, an alkaline earth metal selected from the group consisting of barium, strontium and calcium and a Group VIII metal to dehydroisomerize alkylcyclopentanes. The alkylcyclopentanes are contacted with a catalyst comprising a large-pore zeolite (preferably type L zeolite), at least one Group VIII metal (preferably platinum); and an alkaline earth metal selected from the group consisting of barium, strontium and calcium (preferably barium).

Preferably, the catalyst contains: (a) a type L zeolite containing from 0.1% to 5% by weight platinum (preferably from 0.1% to 1.5% by weight platinum) and 0.1% to 40% by weight barium (preferably from 0.1% to 35% by weight barium, more preferably from 1% to 20% by weight barium); and (b) an inorganic binder. The majority of the type L zeolite crystals are preferably greater than 500 Angstroms, more preferably greater than 1000 Angstroms. In the most preferred embodiment, at least 80% of the crystals of type L zeolite are greater than 1000 Angstroms. The inorganic binder is preferably either a silica, alumina, or an aluminosilicate. The alkylcyclopentanes are contacted with the barium-exchanged type zeolite at a temperature of from 800° to 1000° F. (preferably 820° to 950° F.); an LHSV of from 0.1 to 20 (preferably from 0.5 to 10); a pressure of from 0 to 500 psig (preferably from 1 atm. to 300 psig); and an $H_2$/HC ratio of from 0 to 20 (preferably from 1 to 10).

DESCRIPTION OF THE PREFERRED EMBODIMENTS

In its broadest aspect, the present invention involves a catalyst comprising a large-pore zeolite, an alkaline earth metal and a Group VIII metal and its use in the dehydroisomerization of alkylcyclopentanes.

Dehydroisomerization Reaction

According to the present invention, the alkylcyclopentane is contacted with the catalyst in a dehydroisomerization zone maintained at dehydroisomerization conditions. This contacting may be accomplished by using the catalyst in a fixed bed system, a moving bed system, a fluidized system, or in a batch-type operation; however, in view of the danger of attrition losses of the valuable catalyst and of well-known operational advantages, it is preferred to use either a fixed bed system or a dense-phase moving bed system. It is also contemplated that the contacting step can be performed in the presence of a physical mixture of particles of a conventional dual-function catalyst of the prior art. In a fixed bed system, the alkylcyclopentane is preheated by any suitable heating means to the desired reaction temperature and then passed into a dehydroisomerization zone containing a fixed bed of the catalyst. It is, of course, understood that the dehydroisomerization zone may be one or more separate reactors with suitable means therebetween to ensure that the desired conversion temperature is maintained at the entrance to each reactor. It is also important to note that the reactants may be contacted with the catalyst bed in either upward, downward, or radial flow fashion with the latter being preferred. In addition, the reactants may be in a liquid phase, a mixed liquid-vapor phase, or a vapor phase when they contact the catalyst, with best results obtained in the vapor phase. The dehydroisomerization system then preferably comprises a dehydroisomerization zone containing one or more fixed beds or dense-phase moving beds of the catalyst. In a multiple bed system, it is, of course, within the scope of the present invention to use the present catalyst in less than all of the beds with a conventional dual-function catalyst being used in the remainder of the beds. The dehydroisomerization zone may be one or more separate reactors with suitable heating means therebetween to compensate for the endothermic nature of the dehydroisomerization reaction that takes place in each catalyst bed.

Although hydrogen is the preferred diluent for use in the subject dehydrosiomerization method, in some cases other art-recognized diluents may be advantageously utilized, either individually or in admixture with hydrogen, such as $C_1$ to $C_5$ paraffins such as methane, ethane, propane, butane and pentane; the like diluents, and mixtures thereof. Hydrogen is preferred because it serves the dual function of not only lowering the partial pressure of the alkylcyclopentane, but also of suppressing the formation of hydrogen-deficient, carbonaceous deposits (commonly called coke) on the catalystic composite. Ordinarily, hydrogen is utilized in amounts sufficient to insure a hydrogen to hydrocarbon mole ratio of about 0 to 20, with best results obtained in the range of about 1 to 10. The hydrogen charged to the dehydroisomerization zone will typically be contained in a hydrogen-rich gas stream recycled from the effluent stream from this zone after a suitable gas/liquid separation step.

The dehydroisomerization conditions used in the present method include a reactor pressure which is selected from the range of about 0 to 500 psig, with the preferred pressure being about 1 atm. to 300 psig. The temperature of the dehydroisomerization is preferably about 820° to 950° F. As is well known to those skilled in the dehydroisomerization art, the initial selection of the temperature within this broad range is made primarily as a function of the desired conversion level of the alkylcyclopentane considering the characteristics of the catalyst. Ordinarily, the temperature then is thereafter slowly increased during the run to compensate for the inevitable deactivation that occurs to provide a relatively constant value for conversion.

The liquid hourly space velocity (LHSV) used in the instant dehydroisomerization method is selected from the range of 0.1 to 20 hrs.$^{-1}$, with a value in the range of 0.5 to 10 hrs.$^{-1}$ being preferred.

If, after a period of operation, the catalyst has become deactivated by the presence of carbonaceous deposits, said deposits can be removed from the catalyst by passing an oxygen-containing gas, such as air, into contact with the catalyst at an elevated temperature in order to burn the carbonaceous deposits from the catalyst. The method of regenerating the catalyst will depend on whether there is a fixed bed, moving bed, or fluidized bed operation. Regeneration methods and conditions are well known in the art.

The Catalyst

The catalyst according to the invention is a large-pore zeolite charged with Group VIII metal and an alkaline earth metal.

The catalyst according to the invention is a large-pore zeolite charged with one or more dehydrogenating constituents. The term "large-pore zeolite" is defined as a zeolite having an effective pore diameter of 6 to 15 Angstroms.

Among the large-pored crystalline zeolites which have been found to be useful in the practice of the present invention, type L zeolite, zeolite X, and zeolite Y are the most important and have apparent pore sizes on the order of 7 to 9 Angstroms.

The chemical formula for zeolite Y expressed in terms of mole oxides may be written as:

$$(0.7-1.1)Na_2O:Al_2O_3:xSiO_2:yH_2O$$

wherein x is a value greater than 3 up to about 6 and y may be a value up to about 9. Zeolite Y has a characteristic X-ray powder diffraction pattern which may be employed with the above formula for identification. Zeolite Y is described in more detail in U.S. Pat. No. 3,130,007. U.S. Pat. No. 3,130,007 is hereby incorporated by reference to show a zeolite useful in the present invention.

Zeolite X is a synthetic crystalline zeolitic molecular sieve which may be represented by the formula:

$$(0.7-1.1)M_{2/n}O:Al_2O_3:(2.0-3.0)SiO_2:yH_2O$$

wherein M represents a metal, particularly alkali and alkaline earth metals, n is the valence of M, and y may have any value up to about 8 depending on the identity of M and the degree of hydration of the crystalline zeolite. Zeolite X, its X-ray diffraction pattern, its properties, and method for its preparation are described in detail in U.S. Pat. No. 2,882,244. U.S. Pat. No. 2,882,244 is hereby incorporated by reference to show a zeolite useful in the present invention.

The preferred catalyst according to the invention is a type L zeolite charged with one or more dehydrogenating constituents.

Type L Zeolite

Type L zeolites are synthetic zeolites. A theoretical formula is $Mg/n\ [(AlO_2)_9(SiO_2)_{27}]$ in which M is a cation having the valency n.

The real formula may vary without changing the crystalline structure; for example, the mole ratio of silicon to aluminum (Si/Al) may vary from 1.0 to 3.5

Although there are a number of cations that may be present in zeolite L, in one embodiment, it is preferred to synthesize the potassium form of the zeolite, i.e, the form in which the exchangeable cations present are substantially all potassium ions. The reactants accordingly employed are readily available and generally water soluble. The exchangeable cations present in the zeolite may then conveniently be replaced by other exchangeable cations, as will be shown below, thereby yielding isomorphic form of zeolite L.

In one method of making zeolite L, the potassium form of zeolite L is prepared by suitably heating an aqueous metal aluminosilicate mixture whose composition, expressed in terms of the mole ratios of oxides, falls within the range:

$K_2O/(K_2O+Na_2O)$: From about 0.33 to about 1
$(K_2O+Na_2O)/SiO_2$: From about 0.35 to about 0.5
$SiO_2/Al_2O_3$: From about 10 to about 28
$H_2O/(K_2O+Na_2O)$: From about 15 to about 41

The desired product is hereby crystallized out relatively free from zeolites of dissimilar crystal structure.

The potassium form of zeolite L may also be prepared in another method along with other zeolitic compounds by employing a reaction mixture whose composition, expressed in terms of mole ratios of oxides, falls within the following range:

$K_2O/(K_2O+Na_2O)$: From about 0.26 to about 1
$(K_2O+Na_2O)/SiO_2$: From about 0.34 to about 0.5
$SiO_2/Al_2O_3$: From about 15 to about 28
$H_2O/(K_2O+Na_2O)$: From about 15 to about 51

It is to be noted that the presence of sodium in the reaction mixture is not critical to the present invention.

When the zeolite is prepared from reaction mixtures containing sodium, sodium ions are generally also included within the product as part of the exchangeable cations together with the potassium ions. The product obtained from the above ranges has a composition, expressed in terms of moles of oxides, corresponding to the formula:

$$0.9-1.3[(1-x)K_2O, xNa_2O]:Al_2O_3:5.2-6.9SiO_2:yH_2O$$

wherein "x" may be any value from 0 to about 0.75 and "y" may be any value from 0 to about 9.

In making zeolite L, representative reactants are activated alumina, gamma alumina, alumina trihydrate and sodium aluminate as a source of alumina. Silica may be obtained from sodium or potassium silicate, silica gels, silicic acid, aqueous colloidal silica sols and reactive amorphous solid silicas. The preparation of typical silica sols which are suitable for use in the process of the present invention are described in U.S. Pat. No. 2,574,902 and U.S. Pat. No. 2,597,872. Typical of the group of reactive amorphous solid silicas, preferably having an ultimate particle size of less than 1 micron, are such materials as fume silicas, chemically precipitated and precipitated silica sols. Potassium and sodium hydroxide may supply the metal cation and assist in controlling pH.

In making zeolite L, the usual method comprises dissolving potassium or sodium aluminate and alkali, viz., potassium or sodium hydroxide, in water. This solution is admixed with a water solution of sodium silicate, or preferably with a water-silicate mixture derived at least in part from an aqueous colloidal silica sol. The resultant reaction mixture is placed in a container made, for example, of metal or glass. The container should be closed to prevent loss of water. The reaction mixture is then stirred to insure homogeneity.

The zeolite may be satisfactorily prepared at temperatures of from about 90° C. to 200° C. the pressure being atmospheric or at least that corresponding to the vapor pressure of water in equilibrium with the mixture of reactants at the higher temperature. Any suitable heating apparatus, e.g., an oven, sand bath, oil bath or jacketed autoclave, may be used. Heating is continued until the desired crystalline zeolite product is formed. The zeolite crystals are then filtered off and washed to separate them from the reactant mother liquor. The zeolite crystals should be washed, preferably with distilled water, until the effluent wash water, in equilibrium with the product, has a pH of between about 9 and 12. As the zeolite crystals are washed, the exchangeable cation of the zeolite may be partially removed and is believed to be replaced by hydrogen cations. If the washing is discontinued when the pH of the effluent wash water is between about 10 and 11, the $(K_2O+Na_2O)/Al_2O_3$ molar ratio of the crystalline product will be approximately 1.0. Thereafter, the zeolite crystals may be dried, conveniently in a vented oven.

Zeolite L has been characterized in "Zeolite Molecular Sieves" by Donald W. Breck, John Wiley & Sons, 1974, as having a framework comprising 18 tetrahedra unit cancrinite-type cages linked by double 6-rings in columns and crosslinked by single oxygen bridges to form planar 12-membered rings. These 12-membered rings produce wide channels parallel to the c-axis with no stacking faults. Unlike erionite and cancrinite, the cancrinite cages are symmetrically placed across the double 6-ring units. There are four types of cation locations: A in the double 6-rings, B in the cancrinite-type cages, C between the cancrinite-type cages, and D on the channel wall. The cations in site D appear to be the only exchangeable cations at room temperature. During dehydration, cations in site D probably withdraw from the channel walls to a fifth site, site E, which is located between the A sites. The hydrocarbon sorption pores are approximately 7 to 8 Angstroms in diameter.

A more complete description of these zeolites is given, e.g., in U.S. Pat. No. 3,216,789 which, more particularly, gives a conventional description of these zeolites. U.S. Pat. No. 3,216,789 is hereby incorporated by reference to show a type L zeolite useful in the present invention.

Various factors have an effect on the X-ray diffraction pattern of a zeolite. Such factors include temperature, pressure, crystal size, impurities, and type of cations present. For instance, as the crystal size of the type L zeolite becomes smaller, the X-ray diffraction pattern becomes broader and less precise. Thus, the term "zeolite L" includes any zeolites made up of cancrinite cages having an X-ray diffraction pattern substantially similar to the X-ray diffraction patterns shown in U.S. Pat. No. 3,216,789.

Crystal size also has an effect on the selectivity of the catalyst. For reasons not yet fully understood, catalysts having at least 80% of the crystals of the type L zeolite larger than about 1000 Angstroms give longer run length than catalysts having substantially all of the crystals of the type L zeolite between 200 and 500 Angstroms. Thus, large crystal-size type L zeolite is the preferred support.

Type L zeolites are conventionally synthesized largely in the potassium form, i.e., in the theoretical formula given previously, most of the M cations are potassium. The M cations are exchangeable, so that a given type L zeolite, e.g., a type L zeolite in the potassium form, can be used to obtain type L zeolites containing other cations, by subjecting the type L zeolite to ion exchange treatment in an aqueous solution of appropriate salts. However, it is difficult to exchange all of the original cations, e.g., potassium, since some exchangeable cations in the zeolite are in sites which are difficult for the reagents to reach.

Alkaline Earth Metals

An essential element of the present invention is the presence of an alkaline earth metal in the type L zeolite. That alkaline earth metal must be either barium, strontium or calcium. Preferably the alkaline earth metal is barium. The alkaline earth metal can be incorporated into the zeolite by synthesis, impregnation or ion exchange. Barium is preferred to the other alkaline earths because the resulting catalyst has high activity, high selectivity and high stability.

In one embodiment, at least part of the alkali metal is exchanged with barium, using techniques known for ion exchange of zeolites. This involves contacting the zeolite with a solution containing excess $Ba^{++}$ ions. The barium should preferably constitute from 0.1% to 35% of the weight of the zeolite, more preferably from 1% to 20% by weight.

Group VIII Metals

The catalysts according to the invention are charged with one or more Group VIII metals, e.g., nickel, ruthenium, rhodium, palladium, iridium or platinum.

The preferred Group VIII metals are iridium, palladium and particularly platinum, which are more selective with regard to dehydroisomerization and are also more stable under the dehydroisomerization reaction conditions than other Group VIII metals.

The preferred percentage of platinum in the catalyst is between 0.1% and 5%, more preferably from 0.1% to 1.5%.

Group VIII metals are introduced into the L zeolite by synthesis, impregnation or exchange in an aqueous solution of an appropriate salt. When it is desired to introduce two Group VIII metals into the zeolite, the operation may be carried out simultaneously or sequentially.

By way of example, platinum can be introduced by impregnating the zeolite with an aqueous solution of tetrammineplatinum (II) nitrate, tetrammineplatinum (II) hydroxide, dinitrodiamino-platinum or tetrammineplatinum (II) chloride. In an ion exchange process, platinum can be introduced by using cationic platinum complexes such as tetrammineplatinum (II) nitrate.

Catalyst Pellets

An inorganic oxide can be used as a carrier to bind the type L zeolite containing the Group VIII metal and alkaline earth metal and give the catalyst additional strength. The carrier can be a natural or a synthetically produced inorganic oxide or combination of inorganic oxides. Preferred loadings of inorganic oxide are from 5% to 25% by weight of the catalyst. Typical inorganic oxide supports which can be used include aluminosilicates (such as clays), alumina, and silica, in which acidic sites are preferably exchanged by cations which do not impart strong acidity.

One preferred inorganic oxide support is "Ludox", which is a colloidal suspension of silica in water, stabilized with a small amount of alkali.

When an inorganic oxide is used as a carrier, there are two preferred methods in which the catalyst can be made, although other embodiments could be used.

In the first preferred embodiment, the type L zeolite is made, then the type L zeolite is ion exchange with a barium solution, separated from the barium solution, dried and calcined, impregnated with platinum, calcined, and then mixed with the inorganic oxide and extruded through a die to form cylindrical pellets. Advantageous methods of separating the type L zeolite from the barium and platinum solutions are by a batch centrifuge or a pressed filter. This embodiment has the advantage that all the barium and platinum are incorporated on the type L zeolite and none are incorporated on the inorganic oxide. It has the disadvantage that the type L zeolite is of small size, which is hard to separate from the barium solution and the platinum solution.

In the second preferred embodiment, the type L zeolite is mixed with the inorganic oxide and extruded through the die to form cylindrical pellets, then these pellets are ion exchanged with a barium solution, separated from the barium solution, impregnated with platinum, separated from the platinum solution, and calcined. This embodiment has the advantage that the pellets are easy to separate from the barium and platinum solutions, but it has the disadvantage that barium and platinum are also deposited on the inorganic oxide carrier which would catalyze undesirble reactions. Thus, the choice of which embodiment is used depends on the trade-off between catalyst selectivity and ease of separation of the catalyst from the barium and platinum solutions.

In a third possible embodiment, the type L zeolite ion exchanged with a barium solution, separated from the barium solution, dried and calcined, mixed with the inorganic oxide and extruded through the die to form cylindrical pellets, then these pellets are impregnated with platinum, separated from the platinum solution, and calcined.

In the extrusion of type L zeolite, various extrusion aids and pore formers can be added. Examples of suitable extrusion aids are ethylene glycol and stearic acid. Examples of suitable pore formers are wood flour, cellulose and polyethylene fibers.

After the desired metal or metals have been introduced, the catalyst is treated in air or diluted $O_2$ at about 260° C. to 500° C. and then reduced in hydrogen at temperatures of from 200° C. to 700° C., preferably 300° C. to 620° C.

At this stage the catalyst is ready for use in the dehydroisomerization process. In some cases however, for example when the metal or metals have been introduced by an ion exchange process, it is preferable to eliminate any residual acidity of the zeolite by treating the catalyst with an aqueous solution of a salt of a suitable alkali or alkaline earth element in order to neutralize any hydrogen ions formed during the reduction of metal ions by hydrogen.

In order to obtain optimum selectivity, temperature should be adjusted so that reaction rate is appreciable, but conversion is less than 98%, as excessive temperature and excess reaction can have an adverse affect on selectivity. Pressure should also be adjusted within a proper range. Too high a pressure will place a thermodynamic (equilibrium) limit on the desired reaction, especially for hexane aromatization, and too low a pressure may result in coking and deactivation.

EXAMPLES

The invention will be further illustrated by the following examples which set forth a particularly advantageous method and composition embodiments. While the examples are provided to illustrate the present invention, they are not intended to limit it.

A methylcyclopentane feed which had been hydrofined to remove sulfur, oxygen and nitrogen was dehydroisomerized at 920° F., 100 psig, 2 LHSV, and 6 $H_2$/HC by a dehydroisomerization catalyst. This catalyst was prepared by (1) ion exchanging a potassium-barium-type L zeolite with a sufficient volume of 0.17 molar barium nitrate solution to contain an excess of barium compared to the ion exchange capacity of the zeolite; (2) drying the resulting barium-exchanged type L zeolite catalyst; (3) calcining the catalyst at 590° C.; (4) impregnating the catalyst with 0.8% platinum using tetrammineplatinum (II) nitrate; (5) drying the catalyst; (6) calcining the catalyst at 260° C.; and (7) reducing the catalyst in hydrogen at 480° C. to 500° C.

The feed contained 73 wt.% methylcyclopentane. The distillation data for the feed was start/148° F., 5%/154° F., 10%/157° F., 30%/159° F., 50%/160° F., 70%/161° F., 90%/165° F., 95%/173° F. and end point/222° F. The feed contained 10 vol.% paraffins, 80 vol.% naphthenes, and 10 vol.% aromatics. The conversion was 78% after three hours and 82% after twenty hours. The selectivity for dehydroisomerization was 82 mole% after three hours and 86% after twenty hours.

While the present invention has been described with reference to specific embodiments, this application is intended to cover those various changes and substitutions which may be made by those skilled in the art without departing from the spirit and scope of the appended claims.

What is claimed is:

1. A method of dehydroisomerization of alkylcyclopentanes to produce aromatics comprising contacting said alkylcyclopentanes under dehydroisomerization conditions with a catalyst comprising:
   (a) a large-pore zeolite;
   (b) at least one Group VIII metal; and
   (c) an alkaline earth metal selected from the group consisting of barium, strontium and calcium.

2. A method of dehydroisomerization of alkylcyclopentanes to produce aromatics according to claim 1 wherein said alkaline earth metal is barium and said Group VIII metal is platinum.

3. A method of dehydroisomerization of alkylcyclopentanes to produce aromatics according to claim 2 wherein said large-pore zeolite has an apparent pore size of from 7 to 9 Angstroms.

4. A method of dehydroisomerization of alkylcyclopentanes to produce aromatics according to claim 3 wherein said catalyst has from 0.1% to 5% by weight platinum and from 0.1% to 35% by weight barium.

5. A method of dehydroisomerization of alkylcyclopentanes to produce aromatics according to claim 4 wherein said large-pore zeolite is selected from the group consisting of zeolite X, zeolite Y and type L zeolite.

6. A method of dehydroisomerization of alkylcyclopentanes to produce aromatics according to claim 5 wherein said large-pore zeolite is zeolite Y.

7. A method of dehydroisomerization of alkylcyclopentanes to produce aromatics according to claim 5 wherein said large-pore zeolite is a type L zeolite.

8. A method of dehydroisomerization of alkylcyclopentanes to produce aromatics according to claim 7 wherein said catalyst has from 0.1% to 20% by weight barium.

9. A method of dehydroisomerization of alkylcyclopentanes to produce aromatics according to claim 8 wherein the majority of the crystals of said type L zeolite are larger than 500 Angstroms.

10. A method of dehydroisomerization of alkylcyclopentanes to produce aromatics according to claim 9 wherein the majority of the crystals of said type L zeolite are large than 1000 Angstroms.

11. A method of dehydroisomerization of alkylcyclopentanes to produce aromatics according to claim 10 wherein at least 80% of the crystals of said type L zeolite are larger than 1000 Angstroms.

12. A method of dehydroisomerization of alkylcyclopentanes to produce aromatics according to claim 11 wherein said catalyst comprises:
  (a) a type L zeolite containing from 0.1% to 1.5% by weight platinum and from 1% to 20% by weight barium; and
  (b) an inorganic binder.

13. A method of dehydroisomerization of alkylcyclopentanes to produce aromatics according to claim 12 wherein said inorganic binder is selected from the group consisting of silica, alumina, and aluminosilicates.

14. A method of dehydroisomerization of alkylcyclopentanes to produce aromatics according to claim 8 wherein said contacting occurs at a temperature of from 800° to 1000° F.; an LHSV of from 0.1 to 20; a pressure of from 0 to 500 psig; and an $H_2$/HC ratio of from 0 to 20.

15. A method of dehydroisomerization of alkylcyclopentanes to produce aromatics according to claim 14 wherein said contacting occurs at a temperature of from 820° to 950° F.; an LHSV of from 0.5 to 10; a pressure of from 1 atm., to 300 psig; and an $H_2$/HC ratio of from 1 to 10.

* * * * *

UNITED STATES PATENT AND TRADEMARK OFFICE
CERTIFICATE OF CORRECTION

PATENT NO. : 4,434,311

DATED : February 28, 1984

INVENTOR(S) : WALDEEN C. BUSS, et al.

It is certified that error appears in the above-identified patent and that said Letters Patent are hereby corrected as shown below:

TITLE:

"CONVERSION OF ALKYCYCLOPENTANES TO AROMATICS" should read --CONVERSION OF ALKYLCYCLOPENTANES TO AROMATICS--

Col. 1, line 51, "aromatics" should read --aromatic--

Col. 1, line 62, "given" should read --give--

Col. 2, line 29, "numer" should read --number--

Col. 5, line 45, "Mg/n" should read --M$_9$/n

Col. 9, line 9, "would" should read --could--

Col. 9, line 9, "undesirble" should read --undesirable--

Signed and Sealed this

Twenty-fifth Day of September 1984

[SEAL]

Attest:

GERALD J. MOSSINGHOFF

Attesting Officer

Commissioner of Patents and Trademarks